(12) United States Patent
Goorevich et al.

(10) Patent No.: US 9,131,324 B2
(45) Date of Patent: *Sep. 8, 2015

(54) OPTIMIZING OPERATIONAL CONTROL OF A HEARING PROSTHESIS

(71) Applicant: Cochlear Limited, Macquarie University, NSW (AU)

(72) Inventors: Michael Goorevich, Naremburn (AU); Kyriaky Griffin, Kellyville (AU); Timothy Neal, West Ryde (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/101,520

(22) Filed: Dec. 10, 2013

(65) Prior Publication Data

US 2014/0172042 A1    Jun. 19, 2014

Related U.S. Application Data

(63) Continuation of application No. 12/666,289, filed as application No. PCT/AU2008/000909 on Jun. 20, 2008, now Pat. No. 8,605,923.

(30) Foreign Application Priority Data

Jun. 20, 2007  (AU) ................................ 2007903300

(51) Int. Cl.
*H04R 25/00*  (2006.01)
*A61N 1/36*  (2006.01)

(52) U.S. Cl.
CPC ............ *H04R 25/70* (2013.01); *A61N 1/36032* (2013.01); *H04R 25/505* (2013.01); *H04R 2225/41* (2013.01)

(58) Field of Classification Search
CPC ............ H04R 2225/41; H04R 25/505; H04R 25/554; H04R 25/558; H04R 25/30; H04R 25/50; H04R 25/70; A61N 1/36032
USPC ............... 381/57, 58, 60, 312, 314, 315, 320; 73/585; 600/559
See application file for complete search history.

(56) References Cited

U.S. PATENT DOCUMENTS

| | | | | |
|---|---|---|---|---|
| 4,425,481 | A * | 1/1984 | Mansgold et al. | 381/317 |
| 8,150,044 | B2 * | 4/2012 | Goldstein et al. | 381/57 |
| 2004/0213424 | A1 * | 10/2004 | Hamacher et al. | 381/315 |

* cited by examiner

*Primary Examiner* — Huyen D Le
(74) *Attorney, Agent, or Firm* — McDonnell Boehnen Hulbert & Berghoff LLP

(57) ABSTRACT

A method for operating a hearing prosthesis is provided. A plurality of settings are provided, each setting providing a different operating functionality for the hearing prosthesis suitable for different situations. A signal analysis is executed on input signals to the hearing prosthesis. The signal analysis monitors characteristics of a current situation to detect any change and, in the case of detecting change, classifies the current situation into one of a plurality of predefined states. The suitability of the settings is compared with the determined state. One or more optimal choice(s) of setting(s) is identified for the current situation. The one or more optimal choice(s) of setting(s) is presented to a user. The user is then allowed to make a selection from the presented choice(s) of setting(s). If a selection is received from the user, the selected setting is executed. A hearing prosthesis is also provided.

20 Claims, 5 Drawing Sheets

OPTIMIZING OPERATIONAL CONTROL OF A HEARING PROSTHESIS

CROSS-REFERENCE TO RELATED APPLICATIONS

This application is a continuation application of U.S. patent application Ser. No. 12/666,289 filed Aug. 6, 2010, now U.S. Pat. No. 8,605,923, which is a national stage application under 35 USC §371(c) of PCT Application No. PCT/AU2008/000909, entitled "A METHOD AND APPARATUS FOR OPTIMISING THE CONTROL OF OPERATION OF A HEARING PROSTHESIS," filed on Jun. 20, 2008, which claims priority from Australian Patent Application No. 2007903300, filed on Jun. 20, 2007. The above applications are hereby incorporated by reference herein.

BACKGROUND

1. Field of the Invention

The present invention relates generally to hearing prostheses, and more particularly, the optimizing operational control of the hearing prosthesis.

2. Related Art

Hearing prostheses come in a wide variety of devices which provide hearing assistance to partially deaf and profoundly deaf users. Examples of hearing prostheses include various configurations of external devices such as behind-the-ear (BTE), in-the-ear (ITE), In-the-canal (ITC), mini in-the-canal (MIC) completely in-the-canal (CIC), and so-called Open-fit devices. Other hearing prostheses include implantable devices such as middle ear implants, bone conduction devices, brainstem implants, cochlear implants and devices that include more than one type of hearing prosthesis such as electro-acoustic hearing prostheses which include a cochlear implant and hearing aid.

A typical cochlear implant has many parameters the values of which determine the configuration of the device. For example, the value of the parameters may define which sound processing algorithm and recipient-preferred functions within a sound processor are to be implemented. Each recipient is unique, requiring customization of some parameters such as Threshold (T) and Comfort (C) levels during fitting to provide optimal speech understanding for each recipient. Other parameters may be freely adjusted by the recipient via a user interface, usually for improving comfort or audibility dependant on the current listening environment, situation or prosthesis configuration. An example of this type of parameter is a sound processor "sensitivity" setting, which is usually turned up in quiet environments or down in loud environments. Depending on which features are available in each device and how a sound processor is configured, the recipient is usually able to select between a number of different settings for certain parameters. These settings are generally provided in the form of a number of selectable programs or program parameters stored in device memory. The act of selecting can often be a difficult task, because recipients (or carriers) do not always understand or know which settings to use in a particular sound environment, situation or system configuration. Furthermore, some user interfaces can be physically difficult for recipients to use, due to control or display sizes, for example.

In a cochlear implant system, a sound processing unit is processing at least one audio signal received by at least one audio input transducer to the system (for example a microphone, telecoil or auxiliary input). The sound processing unit can be externally worn or implanted, or a combination of both. At any one time, the implantee is immersed in a particular sound environment. The sound processing unit is processing that sound according to the rules of a particular, current algorithm or program. When the implantee moves into a different sound environment, the current algorithm or settings of the sound processing unit may not be suitable for this new environment. It is up to the implantee to manually determine and then select the appropriate sound processor settings which are best optimized for the new sound environment. While this selection is not readily intuitive or easy to understand, it is often a problem that the implantee makes the incorrect selection, thereby compromising their speech intelligibility or comfort.

U.S. Pat. No. 6,910,013 discloses a hearing device intended to address some of the issues noted above. The device provides what is called, "Auditory Scene Analysis", which essentially analyses the input audio signal to the device. The analysis attempts to classify the current sound environment in which the user is located. On the basis of the analysis, an optimal setting for operating the hearing device is automatically selected and implemented. While this method overcomes the complication involved in selecting an optimal setting, it is noted that the method can provide a number of undesirable practical problems. Firstly, it should be appreciated that the type of Auditory Scene Analysis proposed is not, in practice, perfect and may not, in fact, prompt the automatic selection and implementation of the setting which is optimal to the particular user. From the perspective of a user, the optimal settings can be a subjective issue depending upon a user's preferences. The Auditory Scene Analysis is inevitably conducting an objective assessment which is not guaranteed to result in the same selection of settings as those preferred by the user or which the user finds comfortable. Hence, the feature can become frustrating to a user. Furthermore, in the fully automated method of U.S. Pat. No. 6,910,013, the analysis is continuously repeating, which can cause the continuous change of implemented settings as the analysis sees fit. The change of settings can be readily perceived by a user. If the change occurs too frequently, the user can experience disorientation and/or discomfort. It is an object of the present invention to provide an alternative method and device for optimizing the control of a hearing prosthesis in different situations.

SUMMARY

In accordance with an aspect of the present invention, a hearing prosthesis is disclosed. The hearing prosthesis comprises: a memory configured to store a plurality of candidate settings, each candidate setting providing a different operating functionality for the hearing prosthesis suitable for different situations; a processor configured to execute a signal analysis on input signals to the hearing prosthesis by: monitoring characteristics of a current situation to detect any change; classifying, in the case of having detected a change, the current situation into one of a plurality of predefined states to obtain a current state, comparing the suitability of the candidate settings with the current state; and identifying one or more of the candidate settings as optimal for the current state; and a user interface configured to present the one or more optimal settings and allowing selection from amongst the optimal settings for execution.

According to a another aspect of the present invention there is provided a method for operating a hearing prosthesis, the method including: providing a plurality of candidate settings, each candidate setting providing a different operating functionality for the hearing prosthesis suitable for different situations; analyzing input signals to the hearing prosthesis, the analyzing including monitoring characteristics of a current situation to detect any change, classifying in the case of detecting change, the current situation into one of a plurality of predefined states to obtain a current state; comparing the suitability of the candidate settings with the current state; identifying one of the candidate setting as optimal for the current state; executing the optimal setting and presenting the candidate setting including the optimal setting to a user.

According to a another aspect of the present invention there is a method for operating a hearing prosthesis, the method comprises providing a plurality of candidate settings, each candidate setting providing a different operating functionality for the hearing prosthesis suitable for different situations; receiving a request from a user to update a current setting of the hearing prosthesis; analyzing input signals to the hearing prosthesis, the analyzing including: obtaining characteristics of a current situation; classifying the current situation into one of a plurality of predefined states to obtain a current state; comparing the suitability of the candidate settings with the current state; and identifying one of the candidate settings as optimal for the current state; and executing the optimal setting thereby updating the current setting.

BRIEF DESCRIPTION OF THE DRAWINGS

An illustrative embodiment of the present invention will be described with reference to the accompanying figures, in which.

DETAILED DESCRIPTION

Aspects of the present invention may be implemented in a variety of ways employing suitable use of hardware and/or software. The embodiments illustrated and described are to be considered only illustrative examples. The embodiments are described with reference to use of a cochlear implant system. However, it should be appreciated that the invention can be adapted for use in other hearing prosthesis devices such as hearing aids and implantable hearing devices.

The basic components of a cochlear implant include an audio input transducer, which converts received audio signals into electrical signals; a signal processor, for processing the input signal in accordance with operating parameters dictated by one of a number of selectable settings; a stimulator generator, for converting processed signals into suitable stimulation signals; and an electrode array for applying stimulation to the auditory nerve of the implantee. The various selectable settings may be in the form of various executable programs or sets of parameters for use in a program. The settings could accommodate any specific configuration possible that influences the operation of the hearing instrument, for example: different digital signal and sound processing algorithms, processes and/or operational parameters for these, other types of executable programs (such as system configuration, user interface, etc.), or operational parameters for such programs.

Figure 1:
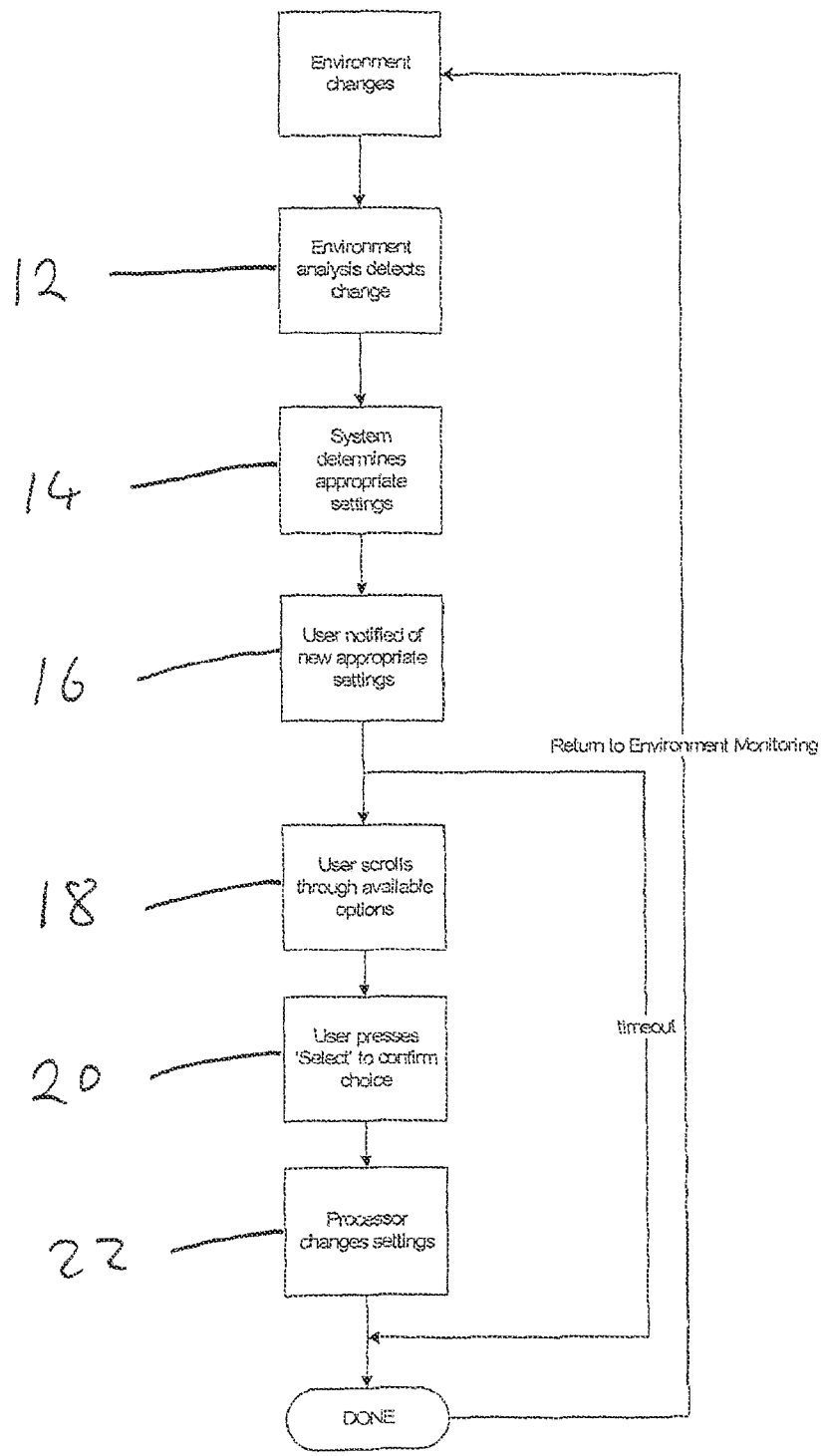
FIG. 1 is a flow chart of the steps involved in providing a user with optimal setting selection according to a first embodiment.
Figure 2:
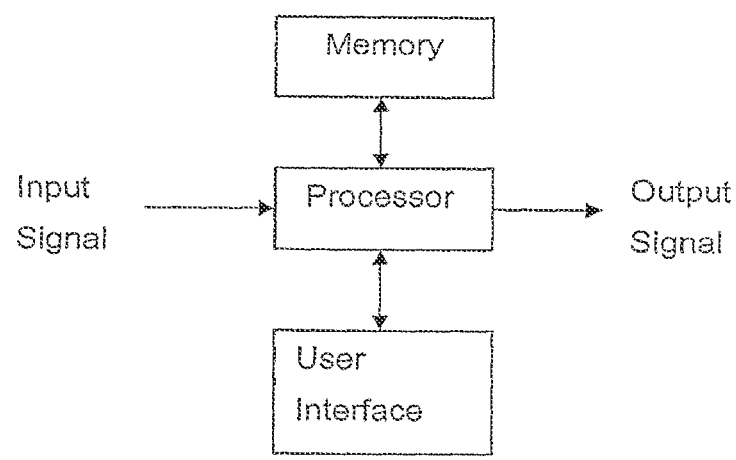
FIG. 2 shows a schematic system diagram of a preferred embodiment.

The settings would be stored in a memory of the system and relate to different optimal settings for different situations in which the implantee may find himself. For the purpose of the first embodiment of the present invention, it is important to provide a "scene analysis" algorithm. The specific nature of the algorithm is, of itself, not essential to the present invention, aside from that it can detect and classify the nature of the sound environment in which the implantee is currently located. In this regard, any suitable algorithm for this purpose, such as that described in U.S. Pat. No. 6,910,013, can be practically employed. Ideally, the algorithm is executed in the system's processor and analyses the received audio signal. The disclosure, particularly relating to the Auditory Scene Analysis (ASA), in U.S. Pat. No. 6,910,013 and the citations referred to therein are herein incorporated by way of reference. The Auditory Scene Analysis (ASA) determines various auditory characteristics from the input audio signal. These characteristics include the loudness, the spectral pattern (timbre), the harmonic structure (pitch), common build-up and decay times (on-/offsets), coherent amplitude modulations, coherent frequency modulations, coherent frequency transitions, binaural effects etc. Detailed descriptions of Auditory Scene Analysis can be found for instance in the articles by A. Bregman, "Auditory Scene Analysis" (MIT Press, 1990) and W. A. Yost, "Fundamentals of Hearing—An Introduction" (Academic Press, 1977). The individual auditory characteristics are described, inter alia, by A. Yost and S. Sheft in "Auditory Perception" (published in "Human Psychophysics" by W. A. Yost, A. N. Popper and R. R. Fay, Springer 1993), by W. M. Hartmann in "Pitch, Periodicity and Auditory Organization" (Journal of the Acoustical society of America, 100 (6), pp 3491-3502, 1996), and by D. K. Mellinger and B. M. Mont-Reynaud in "Scene Analysis" (published in "Auditory Computation" by H. L. Hawkins, T. A. McMullen, A. N. Popper and R. R. Fay, Springer 1996). Referring to FIGS. 1 and 2, the scene analysis algorithm continuously analyses the input audio signal and detects any change in sound environment 12. Upon detecting a change in sound environment, the sound processor then determines which sound processing settings or programs would be most optimal for use in the new environment 14. The list of options determined to be suitable are presented to the implantee via a user interface of the system 16. In this way, the implantee is provided with a list of recommended choices for new settings which can be implemented 18. The implantee is then able to select any one of the options presented via user input means, such as buttons, on the user interface 20. Upon the implantee making a selection, the processor changes its settings to accord with the new setting selected 22. If the implantee does not respond within a predetermined time period, the sound processing unit continues to use the existing settings, e.g. current program and/or current program parameters.

Illustrative examples of situations in which the embodiment would be of practical use include:

Example 1: The system determines that the environment is loud and contains speech in noise. The system proposes to the user that a noise reduction algorithm be selected such as SmartSound Beam, and that the sensitivity be reduced from 12 to 8.

Example 2: The system determines that the environment is loud but contains only noise. The system proposes to the user that a noise reduction algorithm be selected such as SmartSound ASC (in this case sensitivity settings are automatically controlled).

The advantage of this embodiment over prior art systems that provide an automatic scene analysis function (for example in hearing aids) is that the recipient is able to make the final decision as to which settings to use. In hearing instruments incorporating automatic scene analysis, the analysis may make a decision to switch to a parameter set that the recipient does not find comfortable in the given sound environment. Though over-ride functionality may have been provided in some prior art systems, these systems once reverting back to non-automatic mode do not assist the recipient in making a better informed decision on parameter selection. In other words, any practical benefits of the automatic scene analysis become redundant if turned off.

The user interface to the speech processing unit could be a remote control unit with display for either an external or internal sound processing unit, or could be a voice presentation and recognition system for either an external or internal sound processing unit, or could be buttons, rotary switches, displays or any other mechanical interface suitable for external sound processing units, or a combination or some or all of these.

Figure 3:
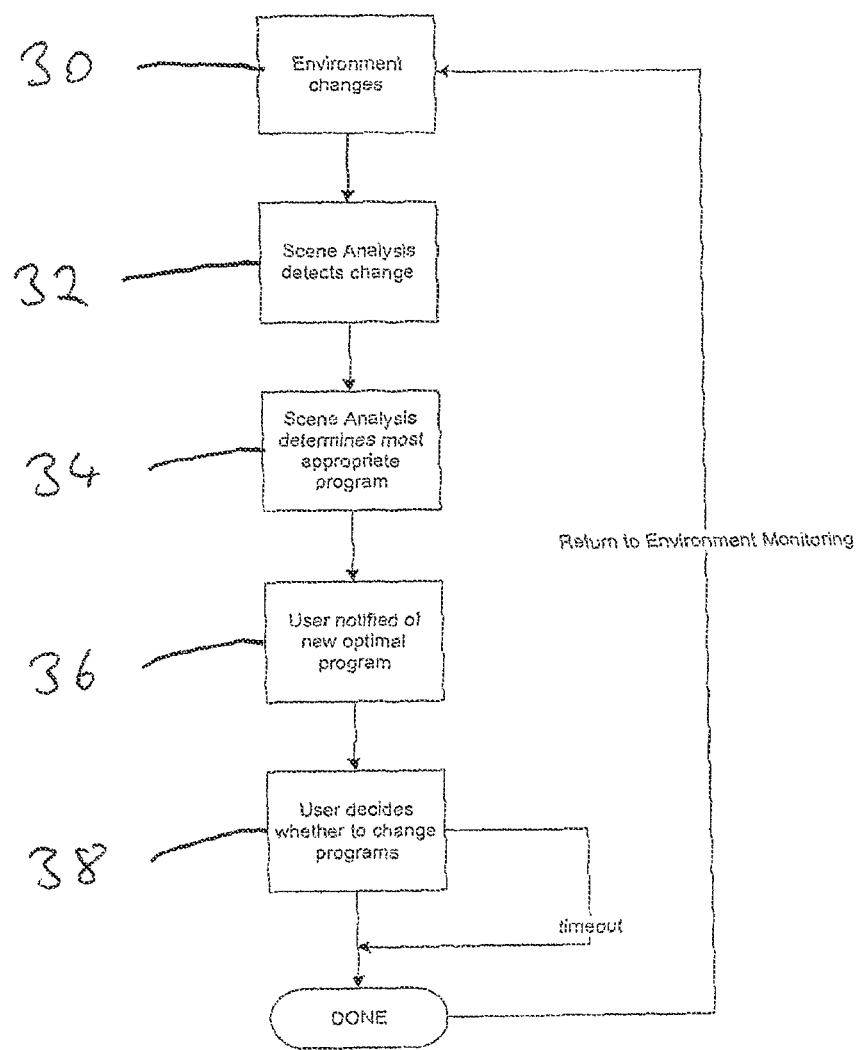
FIG. 3 is a flow chart of the steps involved in an alternative embodiment.

An alternative embodiment is illustrated in FIG. 3. In this system, when the sound environment changes 30, a scene analysis algorithm that is executing in the sound processing unit detects the change in the sound environment 32, and determines which of a pre-determined set of sound processing programs and/or program parameters is most optimal for this new sound environment 34, and notifies the user of the new proposal 36. The user can then choose to accept the suggested setting or not 38. The pre-determined set of settings may be decided during the initial fitting session for the recipient, based on clinical suggestions, defaults or implantee preference (for example, their favorite program in noise). The manner of notification could be via, what is known as, a private beep mechanism—a sequence of beeps that are heard internally by the implantee when the cochlear implant system is trying to notify the recipient about the status of the system.

For example, suppose a cochlear implant system has an external sound processing unit that provides the user with a choice of 4 sound processing programs. When the user selects any of these programs via the user interface of the external sound processing unit, they are presented with a sequence of beeps the moment they make the selection. The number of beeps corresponds to the program number, i.e. if program 1 was selected the user would hear 1 beep, if program 3 was selected the user would hear 3 beeps. In a similar way, if a scene analysis algorithm was executing on the sound processing unit, and it determined that program 2 was the most optimal setting for the given environment, it would issue 2 private beeps to the user. The user then decides whether to accept the suggested program or not. If they do accept, then the user manually makes the corresponding program selection. Alternatively, if the user accepts the suggested program, the system changes directly to that program. If they do not accept within a predefined time interval, then the scene analysis algorithm continues to analyze the sound environment, but no programs or settings are changed.

Another mechanism that can be used to inform the user of the optimal setting could be by playing a segment of speech to the user internally i.e. privately via the electrical stimulation interface of the cochlear implant system. These speech segments could be a phrase informing the user which recommended program to switch to. For example the phrase played to the user could be "program 1" or "switch to program 1" or "map 1" or any other phrase. The speech segments would be stored in memory somewhere in the cochlear implant system. A practical example of such a suitable mechanism suitable is described in US patent application no. 2007/0027676, the disclosure of which is herein incorporated by way of reference.

Figure 4:
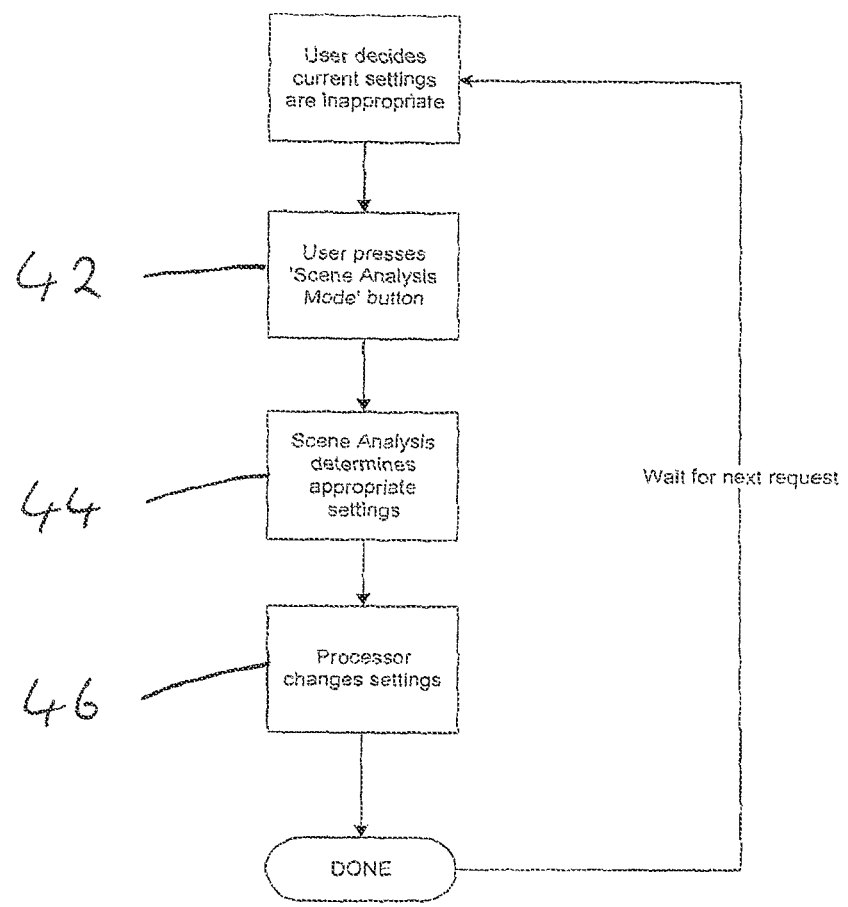
FIG. 4 is a flow chart of the steps involved in another alternative embodiment.

Another alternative embodiment to the system is presented in FIG. 4. In this cochlear implant system, a scene analysis algorithm is available for use by the user, but is not executing. This scene analysis algorithm does not execute in the sound processing unit unless the user initiates the appropriate action to enable the scene analysis algorithm 42. Once the user has enabled the scene analysis algorithm, the scene analysis algorithm determines which sound processing program or parameters are most optimal for the given sound environment 44 and either suggests these to the user via the mechanisms described previously, or automatically selects that setting depending on the preference of the user 46. Any subsequent changes in sound environment are followed by changes to the sound processing setting automatically if the scene analysis algorithm determines that the currently executing setting is no longer optimal. This continues until the recipient decides to disable the scene analysis algorithm. Alternatively, this may be a once-only request.

Alternatively, the scene analysis algorithm is running continuously, but will only report suggestions when prompted to do so by the user. The user may manually act on the suggestions, or the system may automatically implement the suggestions until the user disables the mechanism again.

Figure 5:
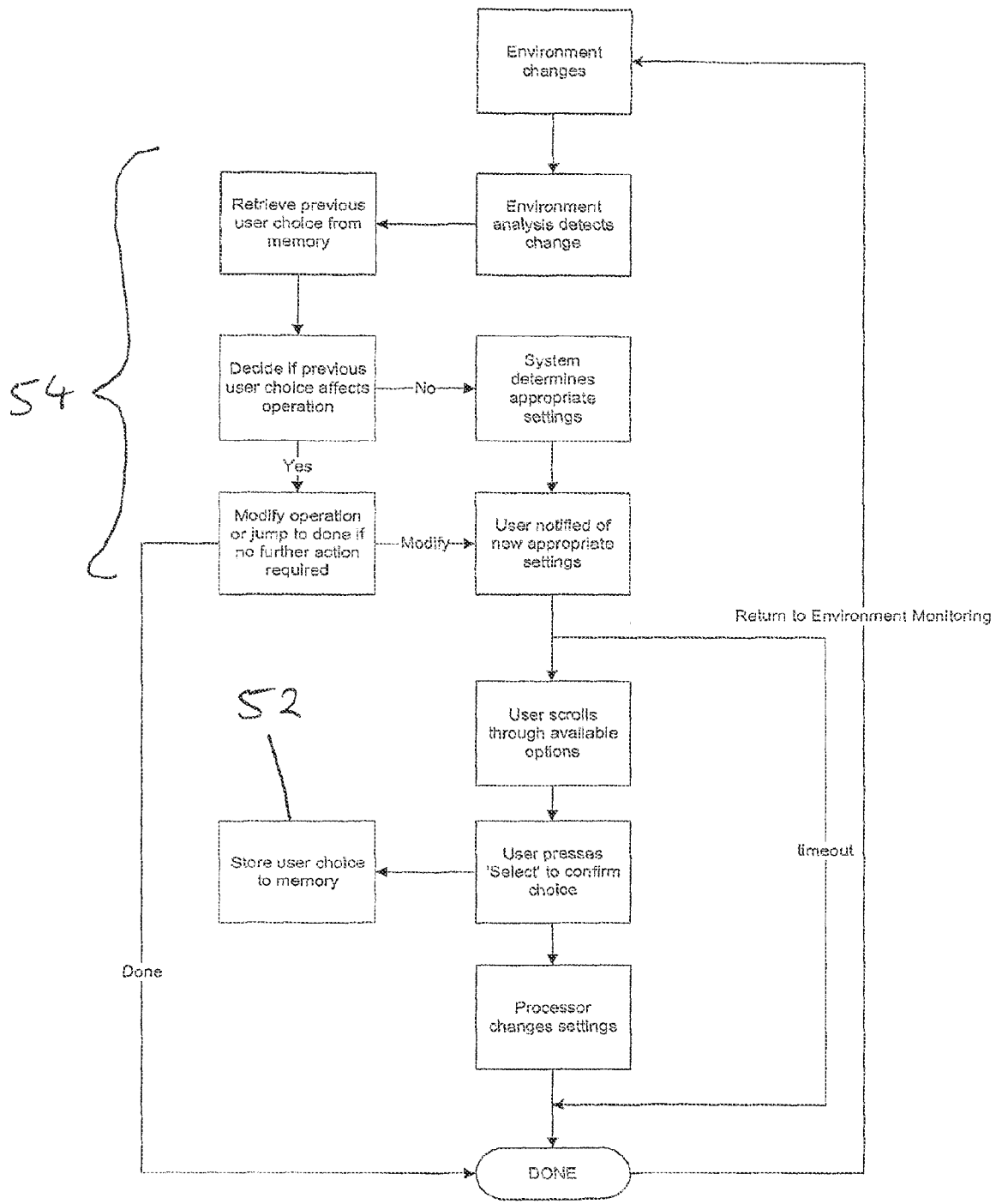
FIG. 5 is a flow chart of the steps involved in a further alternative embodiment.

In an enhanced embodiment of the present invention, as shown in FIG. 5, the system could improve upon its ability to make or highlight appropriate setting suggestions by learning from the user's preferences in the same or similar situations. In this regard, the system would include a learning algorithm and store a log of the user's past selections (or non-selections) 52. This would provide the system with additional criteria to refer to when presenting the user with recommendations. Based upon prior selections, the system would present or highlight, among the options determined to be optimal, the option assumed to be the user's preference 54. For example, the system could be arranged to remember which choices the user does not accept in a particular situation and after a predetermined number of encounters with the particular situation (e.g. five) the system no longer offers such choices in future encounters with the particular situation. Alternatively, the system could be arranged to remember which choice the user consistently selects in a particular situation and after a predetermined number of encounters with the situation (e.g. five) offers this choice as the primary, or possibly only, choice, or could automatically execute this choice. This learning capability could be enhanced by requesting user feedback at the time the user makes a selection. For example, at the time choices of settings are presented to the user, the user could be further presented with feedback options such as: "always offer me only this particular choice when in this environment (when a number of other choices could be offered)", "always immediately select this particular choice automatically when in this environment (when a number of other choices could be offered)", "never offer this particular choice again for this environment", "never make any recommendations in this particular environment", etc.

While the present invention has been described with respect to specific embodiments, it will be appreciated that various modifications and changes could be made without departing from the scope of the invention. Potential variations include system configurations which do not require detection via so-called environmental scene analysis techniques. For each of these possibilities, the system suggests what it determines to be the most optimal settings to the user as described above. Illustrative examples include:

Example 1: The presence of a nearby telephone is detected with a magnetic reed-switch, and the system prompts the user to switch to the telecoil input.

Example 2: The presence of an auxiliary audio input is detected via signal level detection being above a threshold, and the system prompts the user to switch to the aux input.

Example 3: The system detects no signal on the internal microphone, at the same time as a strong signal on the auxiliary input. The system prompts the user to disable mixing on the auxiliary input, disabling the internal microphone and enabling only the aux input.

All documents, patents, journal articles and other materials cited in the present application are hereby incorporated by reference.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A hearing prosthesis, comprising:
a memory configured to store a plurality of candidate settings, each candidate setting providing a different operating functionality for the hearing prosthesis suitable for different situations;
a processor configured to execute a signal analysis on input signals to the hearing prosthesis by monitoring characteristics of a current situation to detect a change and, in response to detecting the change, (i) classifying the current situation into one of a plurality of predefined states to obtain a current state, (ii) comparing a suitability of each of the plurality of candidate settings with the current state, and (iii) identifying from the plurality of candidate settings one or more candidate settings as an optimal setting for the current state; and
a user interface configured to present the one or more optimal settings and to allow a selection from amongst the one or more optimal settings for execution.

2. The hearing prosthesis of claim 1, wherein the user interface includes a remote control unit.

3. The hearing prosthesis of claim 2, wherein the remote control unit includes a graphical display configured to display the one or more optimal settings.

4. The hearing prosthesis of claim 1, wherein the user interface includes a graphical display configured to display the one or more optimal settings.

5. The hearing prosthesis of claim 1, wherein the hearing prosthesis is arranged into at least (i) a first device that includes at least the processor and a second device that includes at least the user interface, wherein the first device and the second device are discrete devices.

6. The hearing prosthesis of claim 5, wherein the second device is a remote control unit.

7. The hearing prosthesis according to claim 1, wherein the hearing prosthesis is a cochlear implant system.

8. The hearing prosthesis according to claim 1, wherein the processor is further configured to continuously execute the signal analysis.

9. The hearing prosthesis according to claim 1, wherein the processor is further configured to automatically execute the signal analysis.

10. The hearing prosthesis according to claim 1, wherein the processor is configured to:
wait, after the one or more optimal settings are presented, for a selection therefrom; and
continue using existing settings when the one or more optimal setting were presented and a maximum amount of time elapses without receiving the selection.

11. A method for operating a hearing prosthesis, the method comprising:
providing a plurality of candidate settings, each candidate setting providing a different operating functionality for the hearing prosthesis suitable for different situations;
analyzing input signals to the hearing prosthesis, the analyzing including monitoring characteristics of a current situation to detect a change and, in response to detecting the change, (i) classifying, the current situation into one of a plurality of predefined states to obtain a current state, (ii) comparing a suitability of each of the plurality of candidate settings with the current state, and (iii) identifying one of the plurality of candidate settings as an optimal setting for the current state;
executing the optimal setting; and
presenting the optimal setting and one or more additional candidate setting included in the plurality of candidate settings.

12. The method according to claim 11, wherein analyzing the input signals further includes executing a scene analysis algorithm for monitoring a current sound environment surrounding the hearing prosthesis.

13. The method according to claim 11, wherein the hearing prosthesis is a cochlear implant system.

14. The method according to claim 11, wherein analyzing the input signals is performed continuously.

15. The method according to claim 11, wherein analyzing the input signals is performed automatically.

16. The method according to claim 11, further comprising:
waiting, after the optimal setting and the one or more additional candidate settings are presented, to receive a selection therefrom;
if the selection is one of the one or more additional settings, executing the selected additional setting; and
if the selection is the optimal setting or a maximum amount of time elapses without receiving the selection, continuing to use the optimal setting.

17. A method for operating a hearing prosthesis, the method comprising:
providing a plurality of candidate settings, each candidate setting providing a different operating functionality for the hearing prosthesis suitable for a different situation;
receiving a request to update a current setting of the hearing prosthesis;
updating the current setting based on the request;
analyzing input signals to the hearing prosthesis, the analyzing including monitoring characteristics of a current situation to detect a change, and, in response to detecting the change, classifying the current situation into one of a plurality of predefined states to obtain a current state, (ii) determining a suitability of the current setting for the current state, and (iii) identifying one of the plurality of candidate settings as an optimal setting for the current state; and
executing the optimal setting, thereby updating the current setting.

18. The method according to claim 17, wherein analyzing the input signals further includes executing a scene analysis algorithm for monitoring a current sound environment in which the hearing prosthesis operates.

19. The method according to claim 17, wherein the hearing prosthesis is a cochlear implant system.

20. The method according to claim 17, wherein the request is received from a remote control unit.

* * * * *